(12) United States Patent
Hoevel et al.

(10) Patent No.: US 6,627,439 B2
(45) Date of Patent: Sep. 30, 2003

(54) ANTIBODIES AGAINST SEMP1(P23)

(75) Inventors: Thorsten Hoevel, Munich (DE); Stefan Koch, Penzberg (DE); Manfred Kubbies, Penzberg (DE); Olaf Mundigl, Polling (DE); Petra Rueger, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/886,683

(22) Filed: Jun. 21, 2001

(65) Prior Publication Data

US 2002/0150574 A1 Oct. 17, 2002

(30) Foreign Application Priority Data

Jun. 23, 2000 (EP) ............................................. 00113344
Apr. 5, 2001 (EP) ............................................. 01107799

(51) Int. Cl.⁷ ............................. C12N 5/16; C07K 16/00
(52) U.S. Cl. ................. 435/326; 530/388.1; 530/388.2; 530/388.8
(58) Field of Search ........................ 530/388.25, 387.3, 530/388.1, 388.8, 388.2; 435/326

(56) References Cited

FOREIGN PATENT DOCUMENTS

| WO | WO 9907850 | 2/1999 |
|---|---|---|
| WO | WO 9907893 | 2/1999 |
| WO | WO99/07893 | * 2/1999 |
| WO | WO 0000609 | 1/2000 |

OTHER PUBLICATIONS

Furuse, M. et al, *J. Cell. Biol.*, 141 (1998) 1539–1550.
Swisshelm, K.A., et al., *GENE*, 226 (1999) 285–295.
Barry, M.A., *Biotechniques*, 16 (1994) 616–618 and 620.
Davis, H.D., *Curr. Opin. Biotechnol.*, 8 (1997) 635–646.
Davis, H.L., *Hum. Mol. Genet.*, 2 (1993) 1847–1851.
Davis, H.L., *Vaccine*, 12 (1994) 1503–1509.
Furuse, M. et al, *J. Cell. Biol.*, 143 (1998) 391–401.
Furuse, M. et al, *J. Cell. Biol.*, 147 (1999) 891–903.
Lowrie, D.B., *Nat. Med.*, 4 (1998) 147–148.
Ulivieri, C., et al, *J. Biotechnol.*, 51 (1996) 191–194.

* cited by examiner

*Primary Examiner*—Christina Chan
*Assistant Examiner*—Maher Haddad
(74) *Attorney, Agent, or Firm*—George W. Johnston; Patricia S. Rocha-Tramaloni; Lyman H. Smith

(57) ABSTRACT

Antibody binding to the SEMP1 antigen and characterized in that said antibody binds to SEMP1 in a manner equivalent to an antibody selected from the group of antibodies DSM ACC2458, DSM ACC2459, DSM ACC2461, and DSM ACC2463 is useful for cancer diagnosis and therapy.

6 Claims, 7 Drawing Sheets

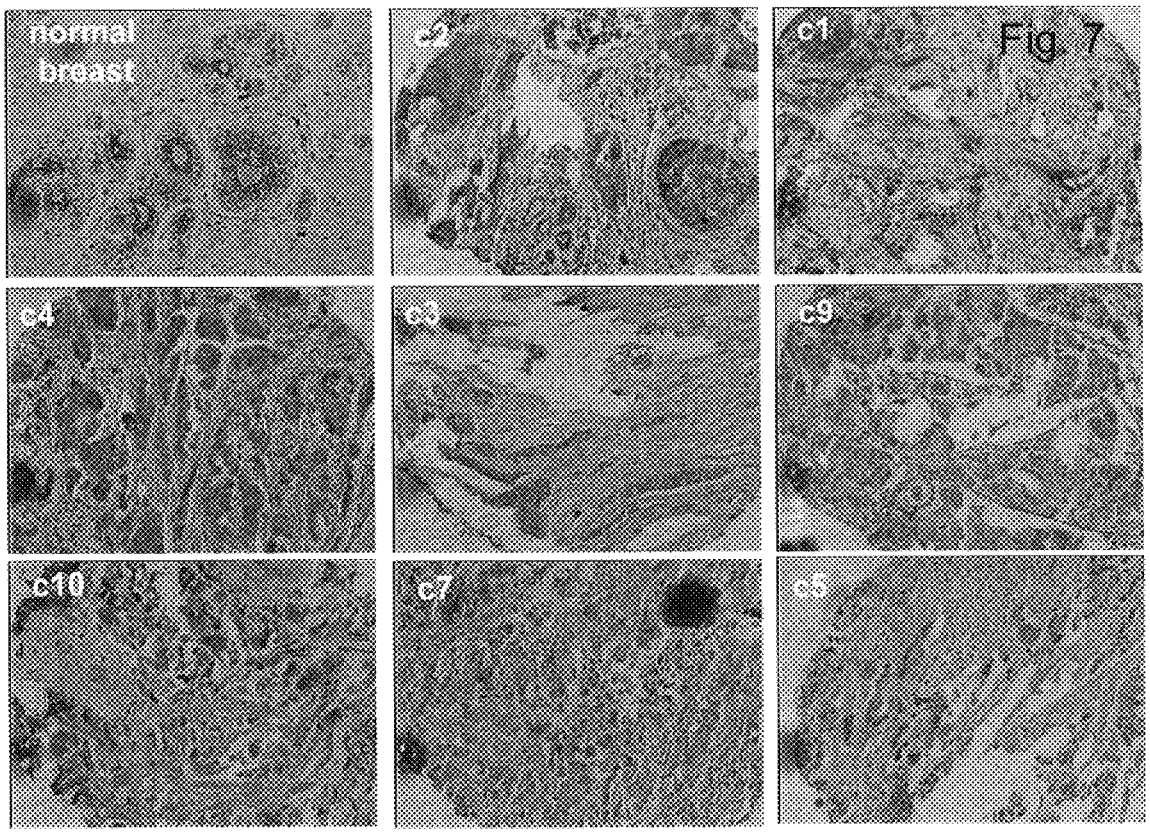

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:fragment of
      CDS of SEQ ID NO:3

<400> SEQUENCE: 1

Gln Trp Arg Ile Tyr Ser Tyr Ala Gly Asp
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:fragment of
      CDS of SEQ ID NO:3

<400> SEQUENCE: 2

Met Lys Cys Met Lys Cys Leu Glu Asp Asp Glu Val Gln Lys Met
1               5                   10                  15

<210> SEQ ID NO 3
<211> LENGTH: 3443
```

```
<212> TYPE: DNA
<213> ORGANISM: Homo sapiens
<220> FEATURE:
<221> NAME/KEY: CDS
<222> LOCATION: (221)..(853)

<400> SEQUENCE: 3
gagcaacctc agcttctagt atccagactc cagcgccgcc ccgggcgcgg accccaaccc      60
cgacccagag cttctccagc ggcggcgcag cgagcagggc tccccgcctt aacttcctcc     120
gcggggccca gccaccttcg ggagtccggg ttgcccacct gcaaactctc cgccttctgc     180
acctgccacc cctgagccag cgcgggcgcc cgagcgagtc atg gcc aac gcg ggg      235
                                             Met Ala Asn Ala Gly
                                              1               5 ctg cag ctg ttg ggc ttc att ctc gcc ttc ctg gga tgg atc ggc gcc      283
Leu Gln Leu Leu Gly Phe Ile Leu Ala Phe Leu Gly Trp Ile Gly Ala
              10                  15                  20 atc gtc agc act gcc ctg ccc cag tgg agg att tac tcc tat gcc ggc      331
Ile Val Ser Thr Ala Leu Pro Gln Trp Arg Ile Tyr Ser Tyr Ala Gly
          25                  30                  35 gac aac atc gtg acc gcc cag gcc atg tac gag ggg ctg tgg atg tcc      379
Asp Asn Ile Val Thr Ala Gln Ala Met Tyr Glu Gly Leu Trp Met Ser
      40                  45                  50 tgc gtg tcg cag agc acc ggg cag atc cag tgc aaa gtc ttt gac tcc      427
Cys Val Ser Gln Ser Thr Gly Gln Ile Gln Cys Lys Val Phe Asp Ser
 55                  60                  65 ttg ctg aat ctg agc agc aca ttg caa gca acc cgt gcc ttg atg gtg      475
Leu Leu Asn Leu Ser Ser Thr Leu Gln Ala Thr Arg Ala Leu Met Val
 70                  75                  80                  85 gtt ggc atc ctc ctg gga gtg ata gca atc ttt gtg gcc acc gtt ggc      523
Val Gly Ile Leu Leu Gly Val Ile Ala Ile Phe Val Ala Thr Val Gly
                  90                  95                 100 atg aag tgt atg aag tgc ttg gaa gac gat gag gtg cag aag atg agg      571
Met Lys Cys Met Lys Cys Leu Glu Asp Asp Glu Val Gln Lys Met Arg
             105                 110                 115 atg gct gtc att ggg ggt gcg ata ttt ctt ctt gca ggt ctg gct att      619
Met Ala Val Ile Gly Gly Ala Ile Phe Leu Leu Ala Gly Leu Ala Ile
         120                 125                 130 tta gtt gcc aca gca tgg tat ggc aat aga atc gtt caa gaa ttc tat      667
Leu Val Ala Thr Ala Trp Tyr Gly Asn Arg Ile Val Gln Glu Phe Tyr
     135                 140                 145 gac cct atg acc cca gtc aat gcc agg tac gaa ttt ggt cag gct ctc      715
Asp Pro Met Thr Pro Val Asn Ala Arg Tyr Glu Phe Gly Gln Ala Leu
150                 155                 160                 165 ttc act ggc tgg gct gct gct tct ctc tgc ctt ctg gga ggt gcc cta      763
Phe Thr Gly Trp Ala Ala Ala Ser Leu Cys Leu Leu Gly Gly Ala Leu
                 170                 175                 180 ctt tgc tgt tcc tgt ccc cga aaa aca acc tct tac cca aca cca agg      811
Leu Cys Cys Ser Cys Pro Arg Lys Thr Thr Ser Tyr Pro Thr Pro Arg
             185                 190                 195 ccc tat cca aaa cct gca cct tcc agc ggg aaa gac tac gtg               853
Pro Tyr Pro Lys Pro Ala Pro Ser Ser Gly Lys Asp Tyr Val
         200                 205                 210 tgacacagag gcaaaggag aaaatcatgt tgaaacaaac cgaaaatgga cattgagata     913
ctatcattaa cattaggacc ttagaatttt gggtattgta atctgaagta tggtattaca     973
aaacaaacaa acaaacaaaa aacccatgtg ttaaaatact cagtgctaaa catggcttaa    1033
tcttatttta tcttctttcc tcaatatagg agggaagatt ttaccatttg tattactgct    1093
tcccattgag taatcatact caaatggggg aagggtgct ccttaaatat atatagatat     1153
```

-continued

```
gtatatatac atgtttttct attaaaaata gacagtaaaa tactattctc attatgttga      1213
tactagcata cttaaaatat ctctaaaata ggtaaatgta tttaattcca tattgatgaa      1273
gatgtttatt ggtatatttt cttttcgtc cttatataca tatgtaacag tcaaatatca      1333
tttactcttc ttcattagct ttgggtgcct ttgccacaag acctagccta atttaccaag      1393
gatgaattct ttcaattctt catgcgtgcc cttttcatat acttatttta tttttacca      1453 taatcttata gcacttgcat cgttattaag cccttatttg ttttgtgttt cattggtctc      1513
tatctcctga atctaacaca tttcatagcc tacattttag tttctaaagc caagaagaat      1573
ttattacaaa tcagaacttt ggaggcaaat ctttctgcat gaccaaagtg ataaattcct      1633
gttgaccttc ccacacaatc cctgtactct gacccatagc actcttgttt gctttgaaaa      1693
tatttgtcca attgagtagc tgcatgctgt tcccccaggt gttgtaacac aactttattg      1753
attgaatttt taagctactt attcatagtt ttatatcccc ctaaactacc tttttgttcc      1813
ccattcctta attgtattgt tttcccaagt gtaattatca tgcgttttat atcttcctaa      1873
taaggtgtgg tctgtttgtc tgaacaaagt gctagacttt ctggagtgat aatctggtga      1933
caaatattct ctctgtagct gtaagcaagt cacttaatct ttctacctct tttttctatc      1993
tgccaaattg agataatgat acttaaccag ttagaagagg tagtgtgaat attaattagt      2053
ttatattact ctcattcttt gaacatgaac tatgcctatg tagtgtcttt atttgctcag      2113
ctggctgaga cactgaagaa gtcactgaac aaaacctaca cacgtacctt catgtgattc      2173
actgccttcc tctctctacc agtctatttc cactgaacaa aacctacaca catacettca      2233 tgtggttcag tgccttcctc tctctaccag tctatttcca ctgaacaaaa cctacgcaca      2293
taccttcatg tggctcagtg ccttcctctc tctaccagtc tatttccatt cttcagctg       2353 tgtctgacat gtttgtgctc tgttccattt taacaactgc tcttactttt ccagtctgta      2413
cagaatgcta tttcacttga gcaagatgat gtatggaaag ggtgttggca ctggtgtctg      2473
gagacctgga tttgagtctt ggtgctatca atcaccgtct gtgtttgagc aaggcatttg      2533
gctgctgtaa gcttattgct tcatctgtaa gcggtggttt gtaattcctg atcttcccac      2593
ctcacagtga tgttgtgggg atccagtgag atagaataca tgtaagtgtg gttttgtaat      2653
ttgaaaagtg ctatactaag ggaaagaatt gaggaattaa ctgcatacgt tttggtgttg      2713
cttttcaaat gtttgaaaat aaaaaaatgt taagaaatgg gtttcttgcc ttaaccagtc      2773
tctcaagtga tgagacagtg aagtaaaatt gagtgcacta aacgaataag attctgagga      2833
agtcttatct tctgcagtga gtatggccca atgctttctg tggctaaaca gatgtaatgg      2893
gaagaaataa aagcctacgt gttggtaaat ccaacagcaa gggagatttt tgaatcataa      2953
taactcataa ggtgctatct gttcagtgat gccctcagag ctcttgctgt tagctggcag      3013
ctgacgctgc taggatagtt agtttggaaa tggtacttca taataaacta cacaaggaaa      3073
gtcagccacc gtgtcttatg aggaattgga cctaataaat tttagtgtgc cttccaaacc      3133
tgagaatata tgcttttgga agttaaaatt taaatggctt ttgccacata catagatctt      3193
catgatgtgt gagtgtaatt ccatgtggat atcagttacc aaacattaca aaaaatttt       3253 atggcccaaa atgaccaacg aaattgttac aatagaattt atccaatttt gatcttttta      3313
tattcttcta ccacacctgg aaacagacca atagacattt tggggtttta taatgggaat      3373
ttgtataaag cattactctt tttcaataaa ttgtttttta atttaaaaaa aggaaaaaaa      3433
aaaaaaaaaa                                                            3443
```

```
<210> SEQ ID NO 4
<211> LENGTH: 211
<212> TYPE: PRT
<213> ORGANISM: Homo sapiens

<400> SEQUENCE: 4

Met Ala Asn Ala Gly Leu Gln Leu Leu Gly Phe Ile Leu Ala Phe Leu
 1               5                  10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
            115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
            195                 200                 205

Asp Tyr Val
    210
```

ANTIBODIES AGAINST SEMP1(P23)

FIELD OF THE INVENTION

The invention comprises antibodies against the human tight junction protein SEMP1, methods for their production and uses thereof in diagnosis and therapy.

BACKGROUND OF THE INVENTION

The extracellular environment of mammalian cells determines via regulation of cell adhesion and cell proliferation a normal, non-tumorigenic behavior of cells in vivo. Losses of these major control elements are hallmarks of tumorigenesis.

Recently occludin and members of the claudin family have been identified as the major constituents of the cell adhesion complex tight junction. The murine claudin-1 obviously constitutes the major tight junction protein in epithelial cells (Furuse, M., et al., J. Cell Biol. 141 (1998) 1539–1550; Furuse, M., et al., J. Cell Biol. 143 (1998) 391–401), and the human homologue SEMP1 (senescence-associated epithelial membrane protein, Swiss Prot. Acc. No. 095832, CLD1 human) was identified recently by molecular genetic analysis (Swisshelm, K. A., et al., Gene 226 (1999) 285–295). There is ample evidence that tight junction as cell—cell contact and sealing protein might be involved in tumorgenesis (Porvaznik, M., et al., J. Supramol. Struct. 10 (1979) 13–30; Swift, J. G., et al., J. Submicrosc. Cytol. 15 (1983) 799–810; Chochand-Prillet, B., et al., Ultrastruct. Pathol. 22 (1998) 413–420; Soler, A. P., et al., Carcinogenesis 20 (1999) 1425–1431; Woo, P. L., et al., J. Biol. Chem. 274 (1999) 32818–32828). In addition, it has been shown recently that the expression of SEMP1 can be found exclusively in cells and tissue of epithelial origin but it is downregulated or completely lost in human breast cancer tumor cells in vitro (Swisshelm, K. A., et al., Gene 226 (1999) 285–295).

The loss or expression of tight junction proteins or associated molecules in the diagnostic evaluation of tumorigenesis and/or tumor progression or therapeutic intervention in vivo or ex vivo requires polyclonal or monoclonal antibodies. The generation and application of antibodies to identify occludin has been shown successfully in vitro (Furuse, M., et al., J. Cell Biol. 141 (1998) 1539–1550; Furuse, M., et al., J. Cell Biol. 143 (1998) 391–401). However significant difficulties were encountered to generate poly- or monoclonal antibodies against the human SEMP1 or its mouse homologue claudin-1. Disappointing results were also reported to generate monoclonal or polyclonal antibodies against murine claudin-1 (Furuse, M., et al., J. Cell Biol. 141 (1998) 1539–1550).

More recently, one polyclonal antibody was generated in rabbits against the C-terminal intracellular domain of murine claudin-1 protein, which does not cross-react with other related endogenous protein (clone MH25, Zymed Laboratories Inc., 458 Carlton Court, South San Francisco, Calif. 94080, Catalog No. 71-7800, http://www.zymed.com/products/71-7800.html) and one monoclonal antibody was generated against the C-terminal domain of murine claudin-1 in rats (Furuse, M., et al., J. Cell Biol. 147 (1999) 891–903).

BRIEF SUMMARY OF THE INVENTION

The present invention therefore provides polyclonal and monoclonal antibodies which bind to SEMP1 (CLD-1 human) polypeptide in a manner equivalent to an antibody selected from the group consisting of antibodies DSM ACC2458, DSM ACC2459, DSM ACC2461, and DSM ACC2463.

Such an antibody according to the invention does not bind to a considerable extent to the C-terminal intracellular domain of murine claudin-1.

Surprisingly, it was found that though attempts to generate anti-SEMP1 antibodies using SEMP1 polypeptide fragments for immunization failed, it is possible to generate SEMP1 specific antibodies using DNA vaccination, preferably with an additional boost with SEMP1 polypeptide. According to the method of the invention it is now possible to easily provide antibodies against all parts of SEMP1, especially against the extracellular domains, which are useful for modulating signal transducing via SEMP1.

DNA vaccination is possible according to the state of the art. The concept of DNA immunization originated from the observation that naked plasmid DNA injected into muscles of mice resulted in transfection of muscle fibers, expression of the transgene and induction of both a CTL (cytotoxic T cell) and an antibody response (Barry, M. A., et al., Biotechniques 16 (1994) 616–618 and 620; Davis, H. L., et al., Hum. Mol. Genet. 2 (1993) 1847–1851; Davis, H. L., et al., Vaccine 12 (1994) 1503–1509; Davis, H. L., Curr. Opin. Biotechnol. 8 (1997) 635–646; Lowrie, D. B., Nat. Med. 4 (1998) 147–148; Ulivieri, C., et al., J. Biotechnol. 51 (1996) 191–194).

The constructs used for DNA immunization are identical to the ones used for delivery of reporter or therapeutic genes. Basically, any of the established eukaryotic expression vectors can be used. Most DNA immunization vectors comprise a strong viral promoter/enhancer sequence to drive high levels of transgene expression in a wide variety of host cells. Also, a polyadenylation sequence to terminate the expressed RNA is required.

DESCRIPTION OF THE FIGURES

FIG. 7 Staining of SEMP1 protein in different breast tumor tissues from different donors (C1, C2, C3, C4, C5, C7, C9 and C10) compared to normal breast tissue. Staining was as described in FIG. 5.

DETAILED DESCRIPTION OF THE INVENTION

As used herein, the term "do not bind to a considerable extent" means that antibody binding cannot be detected by the conventional methods of detecting such bindings which are known in the prior art. Customarily, immune precipitation is applied to determine the binding. The conventional limit of error in immune precipitation (and thus in the meaning of "do not bind to a considerable extent") is about ≦5%.

As used herein, the term "C-terminus of murine daudin-1" means the C-terminal intracellular domain or a part thereof. This domain consists of amino acids 185–211 of SEQ ID NO: 4.

As used herein, the term "antibody" refers to a protein consisting of one or more polypeptides substantially encoded by antibody genes. The recognized antibody genes include the different constant region genes as well as the myriad antibody variable region genes. Antibodies may exist in a variety of forms, including, for example, Fv, Fab, and F(ab)$_2$ as well as single chains (e.g. Houston et al., PNAS USA 85 (1988) 5879–5883; Bird, R. E., et al., Science 242 (1988) 423–426; and, in general, Hood et al., Immunology, Benjamin N.Y., 2nd edition (1984) and Hunkapiller, T., and Hood, L., Nature 323 (1986) 15–16). Especially antibodies produced in non-human transgenic animals which express human Fc receptors are useful (see WO 99/00010) since such antibodies are quite similar to human antibodies. Preferred antibodies according to the invention are monoclonal antibodies and fragments thereof having the same features in relation to the SEMP1 antigen interaction as an antibody selected from the group consisting of antibodies DSM ACC2458, DSM ACC2459, DSM ACC2461, and DSM ACC2463.

Figure 4:
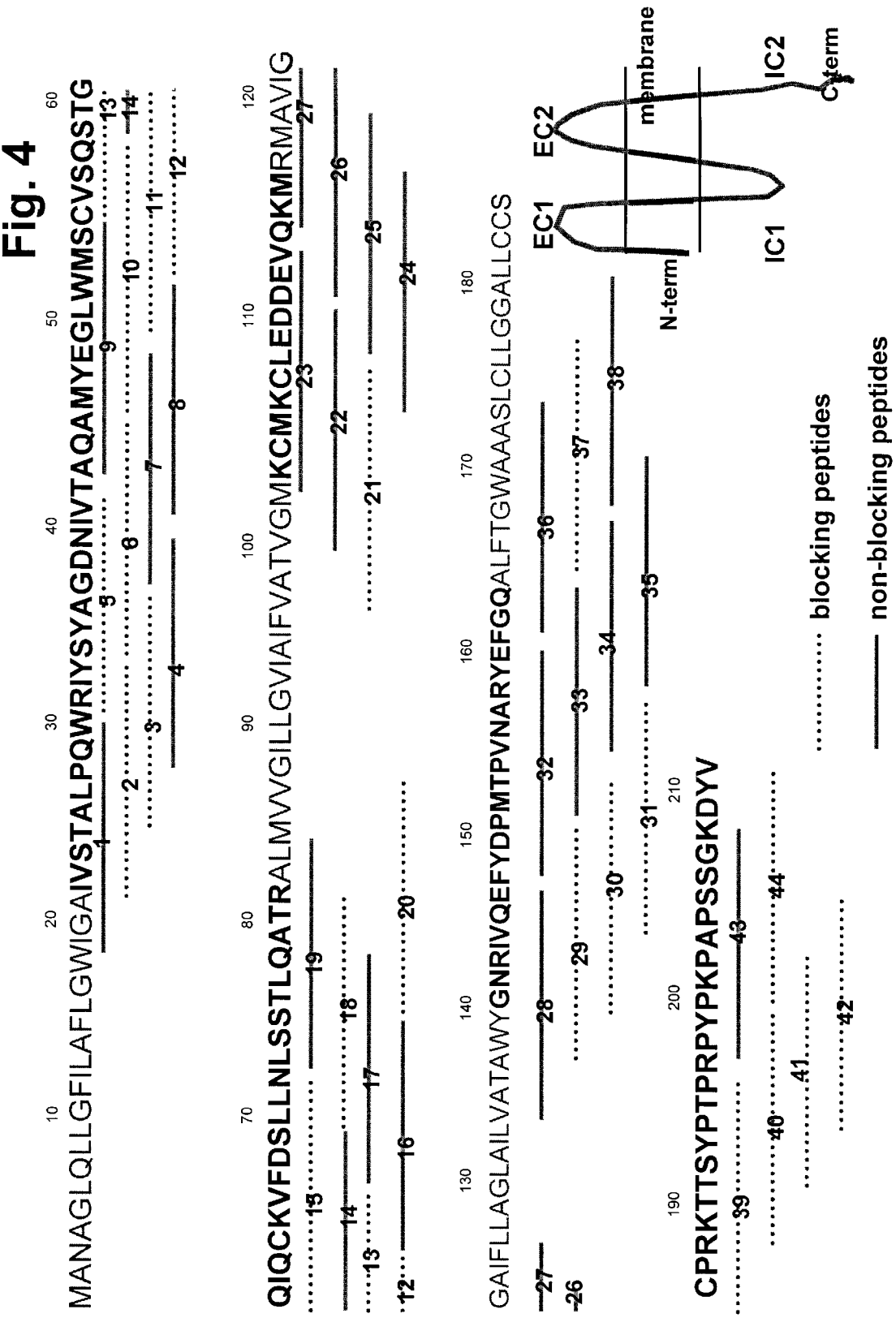
FIG. 4 Domain structure of SEMP1 and epitope mapping of SEMP1 Mab5. Amino acids (aa) 22–81 of SEQ ID NO:4 represent the first extracellular domain (EC1) aa 103–117 represent the first intracellular domain (IC1), aa 141–163 represent the second extracellular domain (EC2), aa 185–211 represent the C-terminal intracellular domain (IC2), aa 1–21 (N-term.), 82–102, 118–140 and 164–184 represent membrane domains.

A further group of antibodies (DSM 2460 and DSM 2462) is directed to the intracellular domain (epitope 2 (IC2), cf. FIG. 4) of SEMP1.

The antibody preferably comprises at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally, the carboxyl terminal portion) which may mediate the binding of the antibody to host tissues or factors including various cells of the immune system, some phagocytic cells and a first component (C1q) of the classical complement system. Typically, the light and heavy polypeptide chains are complete chains, each consisting essentially of a variable region and a complete constant region. The variable regions of the antibody according to the invention can be grafted to constant regions of other isotypes. For example, a polynucleotide encoding the variable region of a heavy chain of the γ1-isotype can be grafted to polynucleotide encoding the constant region of another heavy chain class (or subclass).

Moreover, one to several amino acid substitutions, especially conservative amino acid substitutions, generally can be made to the amino acid sequence of the heavy chain and/or light chain sequences of the present antibodies, without substantially interferring with the antigen binding, and in some embodiments, without substantially increasing the antigenicity of the antibody when injected into a human patient. In some variations, deletions or additions of one to several amino acids can be made. Typically, the amino acid substitutions, additions or deletions are made to constant regions or variable regions, framework sequences and to complementary determining sequences (CDR).

Conservative amino acid substitution is a substitution of an amino acid by a replacement of an amino acid which has similar characteristics (e.g. those with acidic properties: Asp or Glu). A conservative amino acid substitution should not substantially change the structural characteristics of the parent sequence. Examples of such polypeptide structures are described in Proteins, Structures and Molecular Principles, Creighton (editor), W. H. Freeman and Company, New York (1984), Introduction to Protein Structure, C. Brandon and J. Tooze, Garland Publishing, New York (1981), and in Thornton, J. M., et al., Nature 354 (1991) 105–106.

For example, single or multiple amino acid substitutions (preferably conservative amino acid substitutions) may be made in the naturally occurring sequence (preferably in the portion of the polypeptide which does not directly contact antigen).

With the antibodies and methods according to the invention it is possible to find a great number of further antibodies which interact with SEMP1 in an analogous manner. Such antibodies are bindable to SEMP1 antigen in a manner equivalent to the deposited antibodies.

By the term "antibodies bindable in an equivalent manner" there are to be understood antibodies in the case of which an epitope overlapping is detectable with the antibodies in question. The epitope overlapping can be detected with the help of a competitive test system. For this purpose, for example with the help of an enzyme immunoassay there is tested the extent to which the antibody competes with the known antibody for the binding to an immobilized SEMP1 antigen. For this purpose, an appropriately immobilized antigen (e.g. a cell expressing SEMP1 at its surface) is incubated with one of the deposited antibodies in labeled form and an excess of the antibody in question. By detection of the bound labelling there can easily be ascertained the extent to which the antibody in question can displace the definite antibody from the binding. If there is a displacement of at least 20%, preferably at least 50%, at the same concentration or at higher concentrations, preferably in the case of $10^5$-fold excess of the antibody in question, referred to one of the deposited antibodies, then the epitope overlapping is present.

The antibodies can be used as whole polyclonal or monoclonal antibodies, fragments thereof (e.g. Fv, (Fv)$_2$, Fab, Fab', F(ab)$_2$), chimeric, humanized or human antibodies as long as they are binding to SEMP1 in a suitable manner. Short-chain antibody fragments containing only the CDR regions or parts thereof conferring the specific binding to CD30 are also suitable, especially if the antibody is a labeled one. Antibodies of the IgG1 isotype are preferred.

As to production of monoclonal antibodies see, for example, E. Harlow and D. Lane, Antibodies: A Laboratory Manual, Cold Spring Harbor Press (1988); Bessler, W. G., et al., Immunobiol. 170 (1985) 239–244; Jung, G., et al., Angewandte Chemie 97 (1985) 883–885; or Cianfriglia, M., et al., Hybridoma 2 (1993) 451–457.

The present invention also provides a process for the production of antibodies which bind to the SEMP1 antigen, preferably to peptides 1–37, more preferably to peptides 5, 21, 29, 30 and 37 (FIG. 4) mentioned below, wherein a mammalian species is immunized with a SEMP1 DNA plasmid coding for the open reading frame of SEMP1 and subsequently with SEMP1 polypeptide, anti-SEMP1 antibody producing B cells are isolated and fused with myeloma cell lines, the fused cell lines are isolated and tested for antibody activity against SEMP1, the cell lines which produce antibodies that bind to SEMP1 are isolated, monoclonal antibodies (Mabs) are produced from said cell lines and isolated, preferably to substantial purity. Preferably, the immunization is performed over a period of about 3 to 5 months with repeated DNA immunizations at monthly intervals and with a daily boost with SEMP1 polypeptide during about 3 days before isolation of B cells. With the process according to the invention it is possible to produce monoclonal and/or polyclonal antibodies against all immunogenic regions or domains of SEMP1 polypeptide.

Polyclonal antibodies (Paks) are recovered, after such a DNA immunization, according to the state of the art, preferably according to the protocols described in Harlow E. and Lane D., "Antibodies—A Laboratory Manual", Cold Spring Harbor Laboratory (1988).

The present invention also provides derivatives of antibodies according to the present invention, which possess the binding specificity thereof, but with modifications in the region which is not important for the antigen binding. These antibody derivatives can possibly be obtained from antibodies according to the present invention by the exchange of one or more constant domains and/or linkages with other molecules. Thus, for example, an exchange of constant domains for an isotype can be carried out where, for example, an antibody of class IgM can be converted into an antibody of class IgG, with maintenance of its antigen specificity. This isotype switch can take place by cell biological or molecular biological methods which are well-known (see, for example, Rothman, P., et al., Mol. Cell. Biol. 10 (1990) 1672–1679).

There is preferred a process for the production of Mabs with a reduced immunogenicity in humans, wherein variable regions of SEMP1 antibodies are linked to constant regions of a human antibody.

The present invention is also concerned with the use of an antibody according to the present invention for the diagnosis or therapy of, e.g., tumor therapy, angiogenesis control, control of blood brain barrier applying natural or chemical compounds or cells, control of inflammatory response, control of eye pressure, etc. It is thereby preferred to use an antibody selected from the group of antibodies secreted by the cell lines DSM ACC2458, DSM ACC2459, DSM ACC2461, and DSM ACC2463.

Since preferred antibodies obtainable by the process according to the present invention are bindable with surface-bound SEMP1 molecules and especially preferred with the extracellular domain of SEMP1, they are outstandingly suitable for the qualitative or quantitative detection of physiological or pathophysiological expression of the tight junctions. The detection thereby takes place in the known manner by means of an immunological process of determination, preferably by means of an ELISA. Processes of this type are well-known and do not need to be further explained here. The antibodies obtained according to the present invention can thereby be used in labelled and/or immobilized form.

In each case of such immunological method of diagnosis, there is evaluated a signal change following the binding of at least one antibody according to the invention, to which is bound a detectable label.

The diagnostic significance of SEMP1 is preferably the detection of endothelial/epithelial cell layer damage and permeability, identification of starting and/or ongoing tumor cell metastasis, and progression of tumorigenesis.

The present invention also provides a process for improving adjuvants permeability of vaccines, enhancing permeability of endothelial/epithelial tissues to medicals for therapeutic or prophylactic treatment of cancer, acute/chronic inflammatory diseases, myocardial ischemia, artherosclerosis, diabetic retinopathy, rheumatoid arthritis, intestinal infection, wherein there is administered one or a mixture of several antibodies according to the present invention preferably binding to an extracellular domain of SEMP1, optionally together with conventional pharmaceutical carrier, adjuvant, filling or additive materials.

For prevention of an immune response during pharmaceutical application, it is preferred to use antibodies which resemble as closely as possible antibodies of human origin (Glassy, M. C., and Dillman, R. O., Mol. Biother. 1 (1988) 7–13). Preferably, there are used antibodies wherein the variable region of an antibody according to the invention is further modified in that part or all of the SEMP1 binding sequences of said antibody are replaced by the corresponding sequences from a human variable region. Such antibodies are, for example, chimeric or humanized (CDR-grafted) antibodies. Such antibodies usually are manufactured from a rodent monoclonal antibody (see e.g. for review: Morrison, S. L., Annu. Rev. Immunol. 10 (1992) 239–265; Winter, G., and Milstein, C., Nature 349 (1991) 293–299). In a specifically preferred embodiment of the invention, tumour specific human antibodies (Borrebaeck, C. A. K., et al., Proc. Natl. Acad. Sci. USA 85 (1988) 3995–3999; Borrebaeck, C. A. K., Immunol. Today 9 (1988) 355–359) are used for therapeutic purposes. In addition, it is specifically preferred to prepare human Mabs via phage display libraries, as is described, for example, by Griffiths, A. D., et al., EMBO J. 12 (1993) 725–734).

Recombinantly produced SEMP1 antibodies of the invention may be prepared on the basis of the sequence data according to methods known in the art and described in Sambrook et al., Molecular Cloning: A Laboratory Manual, 2nd edition (1989), Cold Spring Harbor, N.Y.; and Berger and Kimmel, Methods in Enzymology, Vol. 152, Guide to Molecular Cloning Techniques (1987), Academic Press Inc., San Diego, Calif. Polynucleotides of the invention are preferably formed from synthetic oligonucleotides.

Such recombinant polypeptides can be expressed in eukaryotic or prokaryotic host cells according to standard methods known in the art; preferably mammalian cells, such as lymphocyte cell lines, may be used as host cells. Typically, such polynucleotide constructs encode a complete human antibody heavy chain and/or a complete human antibody light chain of an antibody according to the invention, heavy and/or light chain variable regions respectively. Alternative human constant region sequences (heavy and/or light chain) can be selected by those of skill in the art from various reference sources, including, but not limited to, those listed in E. A. Kabat et al. (1987) (37). In one embodiment of the invention, a polynucleotide sequence encoding an antibody light chain comprising a human light chain, constant region with an amino terminal peptide linkage (i.e. an inframe fusion) to a variable region of the light chain of an antibody according to the invention and a corresponding heavy chain are expressed and form heavy/light chain dimers and other antibody types.

Since the monoclonal antibodies obtained by the process according to the present invention bind to cell surface-bound SEMP1 antigen which is involved in cell adhesion, they can be used for in vivo treatment in humans. Thus, the present invention also provides a pharmaceutical composition which comprises one or more antibodies according to the present invention, optionally together with conventional pharmaceutical carrier, adjuvant, filling or additive materials. Such a composition according to the invention improves, preferably, adjuvants permeability of vaccines.

For therapeutic uses, a sterile composition containing a pharmacologically effective dosage of one or more antibodies according to the invention is administered to human patient for treating diseases described above. Typically, the composition will comprise a chimeric or humanized antibody which contains the CDR region of an antibody according to the invention for reduced immunogenicity.

The compositions for parenteral administration will commonly comprise a solution of an antibody according to the present invention dissolved in an acceptable carrier, preferably in an aqueous carrier. A variety of aqueous carriers can be used, e.g. water, buffered water, 0.4% saline, 0.3% glycin, and the like. The solutions are sterile and generally of particulate matter. The compositions may be sterilized by conventional well-known techniques. The compositions may contain pharmaceutically acceptable auxiliary substances, such as are required to approximate physiological conditions, such as pH adjusting and buffer agents, toxicity adjusting agents, and the like, for example sodium acetate, sodium chloride, potassium chloride, calcium chloride, sodium lactate, etc. The concentrations of the antibodies according to the invention in these formulations can be varied widely, e.g. from less than about 0.01%, usually at least about 0.1%, to as much as 5% by weight, and will be selected primarily based on fluid volumes, viscosity, etc. or in accordance with the particular mode of administration selected.

Thus, a typical pharmaceutical composition for intramuscular injection could be made up to contain 1 ml sterile buffered water and about 0.1 to 250 mg, preferably 1 to 10 mg of antibody according to the invention.

As mentioned, the antibodies according to the invention can be incorporated into a composition, preferably in a pharmaceutical composition suitable for parenteral administration. Preferably, the antibody will be prepared as an injectable buffered solution containing 0.1 to 500 mg/ml antibody and preferably 0.1 to 250 mg/ml antibody, preferably together with 1 to 500 mmol/l of buffer. The injectable solution can be composed of either a liquid or lyophilized dosage form. The buffer can be, for example, L-histidine (preferably 1 to 50 mM, optimally 5 to 10 mM), at pH 5.0 to 7.0 (optimally pH 6.0).

Other suitable buffers include, but are not limited to, sodium succinate, sodium citrate, sodium phosphate or potassium phosphate. Sodium chloride can be used to modify the toxicity of the solution at a concentration of 0–300 mM (optimally 150 mM for a liquid dosage form). Cryoprotectants can be included for a lyophilized dosage form, principally 0 to 10% sucrose (optimally 0.5 to 1.0%). Other suitable cryoprotectants include trehalose and lactose. Bulking agents can be included for a lyophilized dosage form, principally 1 to 10% mannitol. Stabilizers can be used in both liquid and lyophilized dosage forms, principally 1 to 50 mM L-methionine (optimally 5 to 10 mM).

Other suitable bulking agents include glycine, arginine, can be included as 0–0.05% polysorbate-80 (optimally 0.005–0.01%). Additional surfactants include, but are not limited to, polysorbate 20 and polyoxyethylene ether surfactants such as BRIJ® detergents.

A suitable dosage of the antibody according to the present invention for medical treatments is about 0.01 to 50 mg/kg body weight, whereby this dosage possibly is to be repeatedly administered.

In a preferred embodiment, the pharmaceutical composition includes the antibody at a dosage of about 0.01 mg/kg to 10 mg/kg per application. More preferred dosages of the antibody include 1 mg/kg.

The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Pharmaceutical compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

Prolonged absorption of injectable compositions can be brought about by including in the composition an agent that delays absorption, for example, monostearate salts and oelatin.

The antibodies and antibody portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art, see, e.g., Sustained and Controlled Release Drug Delivery Systems, J. R. Robinson, ed., Marcel Dekker, Inc., New York, 1978.

The antibodies of the present invention are used in liquid, powdered or lyophilized form and may be combined with a suitable diluent or carrier, such as water, a saline, aqueous dextrose, aqueous buffer, and the like. Preservatives may also be added.

The antibodies according to the invention can be lyophilized for storage and reconstituted in a suitable carrier prior to use. Conventional lyophilization and reconstitution techniques can be employed. It will be appreciated by those skilled in the art that lyophilization and reconstitution can lead to varying degrees of biological activity loss and that use levels may have to be adjusted to compensate.

Regardless of the route of administration selected, the antibodies of the present invention are formulated into pharmaceutically acceptable dosage forms by conventional methods known to those skilled in the art. The antibodies may also be formulated using pharmacologically acceptable acid or base addition salts. Moreover, the compounds or their salts may be used in a suitable hydrated form.

Regardless of the route of administration selected, a non-toxic but therapeutically effective quantity of one or more antibodies of this invention is employed in any treatment. The dosage regimen for treating is selected in accordance with a variety of factors including the type, age, weight, sex and medical condition of the patient, type of tumour, the route of administration and the particular antibody employed in the treatment. A physician of ordinary skill can readily determine and prescribe the effective amount of the drug required regarding known antibody therapy approaches. In so proceeding, the physician could employ relatively low doses at first, and subsequently, increased dose until a maximum response is obtained.

The purified SEMP1 polypeptide useful for boosting during immunization can be produced recombinantly in eukaryotic cells. As SEMP1 is a tight junction protein localized at cell—cell contact areas of cells and having a strong tendency of adhesion (Furuse, M., et al., J. Cell. Biol. 147 (1999) 891–903) it is very difficult to isolate and purify the full length polypeptide. In addition, due to the fact that SEMP1 is a membrane-associated protein, it is necessary to release the protein from the membrane. However, several attempts to isolate SEMP1 from cell membranes using different detergents (CHAPS, 3-[(3-cholamidopropyl) dimethylammonio]-1-propane sulfonate; octylglucoside, deoxycholic acid, Igepal®CA630, (octylphenoxy) polyethoxyethanol; Triton®X-100 (octylphenooxy); Thesit, polyoxyethylene-9-lauryl ether; Digitonin) failed. It was, however, surprisingly, possible to isolate and purify further SEMP1 using Zwittergent® (N-dodecyl-N,N-dimethyl-3-ammonio-1-propanesulfonate, Roche Diagnostics GmbH, DE).

Therefore a further aspect of the invention is a method for the chromatographic purification of SEMP1 polypeptide whereby an aqueous composition containing SEMP1 polypeptide applied on a chromatographic column. SEMP1 polypeptide is eluted in the presence of N-dodecyl-N,N-dimethyl-3-ammonio-1-propanesulfonate and recovered from the eluate.

A further aspect of the invention is a method for the release of SEMP1 polypeptide from a matrix like a cell membrane by treating said bound SEMP1 polypeptide in aqueous solution with N-dodecyl in such a manner that SEMP1 polypeptide is solubilized.

The following cell lines mentioned in the present invention which secrete antibodies were deposited by F. Hoffmann-La Roche AG with Deutsche Sammlung von Mikroorganismen und Zellkulturen GmbH (DSM), Mascheroder Weg 1b, D-38124 Braunschweig, Germany, on May 18, 2000:

| Cell Line | Antibody |
| --- | --- |
| DSM ACC2458 | MAB anti-human SEMP1; clone 3 |
| DSM ACC2459 | MAB anti-human SEMP1; clone 4 |
| DSM ACC2460 | MAB anti-human SEMP1; clone 5 |
| DSM ACC2461 | MAB anti-human SEMP1; clone 7 |
| DSM AGC2462 | MAB anti-human SEMP1; clone 38 |
| DSM ACC2463 | MAB anti-human SEMP1; clone 64 |

Their binding characteristics are:

clone 3, competed with peptide 21 (amino acid (aa) 97–108, IC1) and 37 (160–171, EC2)

clone 4, competed with peptide 21 (aa 97–108, IC1)

clone 7, competed with peptide 5 (aa 31–42, EC1)

clone 64, competed with peptide 29 (aa 136–147, EC2), 30 (aa 139–150, EC2) and 31 (aa 142–153, EC2).

clone 5, competed with peptide 41 (aa 191–202,° C.2)

clone 38, competed with peptide 44 (aa 200–211, IC2)

EC1: extracellular epitope 1 (aa 22–81)

IC1: intracellular epitope 1 (aa 103–117)

EC2: extracellular epitope 2 (aa 141–163)

IC2: intracellular epitope 2 (aa 185–211)

(Displayed in brackets are the areas of SEMP1 to which the antibodies bind, confirmed by the 3D computer structure prediction model Signal P (http://genome.cbs.dtu.uk/services/SignalP/), amino acid numbering according to amino acid position of SEMP1 gene product.)

The following examples, the sequence listing and figures are provided to aid the understanding of the present invention, the true scope of which is set forth in the appended claims. It is understood that modifications can be made in the procedures set forth without departing from the spirit of the invention.

SEQ ID NO:1 Fusion peptide.

SEQ ID NO:2 Fusion peptide.

SEQ ID NO:3 SEMP1 DNA sequence.

SEQ ID NO:4 SEMP1 polypeptide sequence.

EXAMPLE 1

Cell culture

Sf9 Insect Cells

For routine passage Sf9 (ATCC CRL 1711) cells were grown in T25 flasks in IPL 41 medium (Gibco) supplemented with 10% serum (Gibco/Yeastolate (Gibco)/Pluronic F-68, Gentamycin (Gibco). For large scale isolation of SEMP1 baculovirus infected Sf9 cells, cells were cultivated in a 7 l batch process fermenter and harvested 3 days after inoculation.

SEMP1 Hybridoma

The anti-SEMP1 secreting hybridoma cells were cultivated in RPMI1640 medium supplemented with 10% FCS/2 mM 1-Glutamin (Roche Molecular Biochemicals)/1× non-essential amino acids (Biochrom AG)/1 mM sodium pyruvate (Biochrom AG) and Nutridoma (Roche Molecular Biochemicals). For generation of anti-SEMP1 enriched hybridoma supernatant, SEMP1 hybridoma clones were inoculated in a Heraeus miniPerm classic, MWCO 12.5 k culture device and the medium was harvested several times a week after cell concentration had reached 1×10E7 cell per ml.

SEMP1 Retrovirus Producer Cell Line AM12

A retrovirus producing, amphotropic cell line HSR BM01 (DSM ACC2235, WO 99/60143) (MoMuLV backbone) transduced with SEMP1 and 1-NGFR (low affinity nerve growth factor receptor), WO 95/06723, was cultivated in DMEM/10% FCS/2 mM 1-Glutamin (Roche Molecular Biochemicals)/1× non-essential amino acids (Biochrom AG)/1 mM sodium pyruvate (Biochrom AG) medium. To obtain a high titer supernatant, fresh medium was added to subconfluent cultures the conditioned supernatant was harvested 24 hrs later (Machl, A. W., Cytometry 29 (1997) 371–374) and immediately used for transduction of cell lines.

MDA-MB 435

The SEMP1 negative MDA-MB 435 human breast cancer cell line as well as its SEMP1 transduced counterpart was cultivated in RPMI/10% FCS/2 mM 1-Glutamin (Roche Molecular Biochemicals)/1× non-essential amino acids (Biochrom AG)/1 mM sodium pyruvate (Biochrom AG). Retroviral SEMP1 transduction was performed by incubation of a subconfluent culture for 24 hrs supernatant containing retroviruses produced according to Example 1c. SEMP1 expressing MDA-MB 435 cell clones were produced by sorting out single cells, binding to FITC labeled antibodies against 1-NGFR from bulk cultures by FACS (FACS Vantage, Becton Dickinson).

EXAMPLE 2

Vector Construction and Expression of SEMP1

The N-terminal hexa-his tagged SEMP1 was cloned by standard procedures into the pBlueBacHis2B vector. Sf9 cells were transfected with the His-SEMP1 plasmid and SEMP1 linearized baculovirus DNA supernatants were harvested 3 days after infection (Invitrogen, Bac'NBlue System). This high titer virus stock was used for re-infection of Sf9 cells. Cells were harvested after a 3 day infection at 27° C. and total protein was extracted by sonification of the Sf9 cells (extraction buffer: 50 mM NaP, 150 mM NaCl, pH 7.2). The protein extract was centrifuged at 30.000 g for 20 min and the pellet was dissolved in 50 mM NaP, 150 mM NaCl, 2% Zwittergent® (N-dodecyl-N,N-dimethyl-3-ammonio-1-propanesulfonate, zwitterionic, Roche Molecular Biochemicals).

Hexa-his tagged SEMP1 was extracted from the crude lysate by affinity chromatography using a Ni-chelate sepharose column (Pharmingen). The column was loaded with 300 mM $NiCl_2$, washed with equilibration buffer (50 mM Tris, 500 mM NaCl, pH 8, 0.5% Zwittergent®), loaded with the crude protein fraction and washed with equilibration buffer/10 mM imidazol. Elution was performed with equilibration buffer/200 mM imidazol. Due to the N-terminal his-tag and enterokinase-tag the size of molecular weight of the modified SEMP1 protein increases from 23 to 27 kD.

EXAMPLE 3

Immunization Procedure

Female BALB/c mice were immunized at 6–8 weeks of age. Prior to immunization, muscle degeneration/regeneration was induced by bilateral intramuscular injection of 100 µl cardiotoxin (10 µM in PBS) (LATOXAN, L-8102; Rosans, France) into the *M. tibialis* (=day 0). 50 µg of plasmid DNA containing the SEMP1 open reading frame purified on a silica-gel-membrane column (Qiagen, DE) in 50 µl sterile 0.9% NaCl was injected intramuscularly into the *M. tibialis* anterior of each hind leg. Five doses of DNA were injected every 4 weeks. Aliquots of serum were taken by retrobulbar puncture at day 97, 3 days prior to dissection of the spleen. The animal displaying the highest serum titer was boosted intravenously with 30 µg SEMP1 protein purified from Sf9 cells (see above). The mice were sacrificed at day 129 and the spleens used to generate hybridomas following standard procedures. High producer hybridoma clones were generated by FACS cell sorter cloning (FACS Vantage, Becton Dickinson) of SEMP1 positive hybridoma bulk cultures.

Anti-SEMP1 Westernblot Analysis

The Western blot analysis was performed by standard procedures using the Novex NuPage Bis-Tris system (Invitrogen). Nitrocellulose membranes blotted from protein gels loaded with different amounts of purified SEMP1 or cell extracts from SEMP1-positive or SEMP1-negative control cells were incubated with supernatants from hybridoma clones producing SEMP1 antibody (1:10 and 1:100 dilution). The anti-SEMP1 signal was detected using standard chemiluminescence protocols (Roche Moleclar Biochemicals).

EXAMPLE 4

Immunofluorescence Microscopy

MDA-MB 435 cells were grown on Poly-L-Lysine (Sigma) coated microscope slides in standard medium at different densities. Cells were washed with PBS and fixed subsequently with 1% paraformaldehyd/PBS for 1 hr at room temperature. Permeabilization and blocking was done with a 1 hr incubation in 0.05% Tween20/10% Albumin (Roche Diagnostics GmbH, DE)/PBS. Thereafter indirect immunofluorescence staining was performed with anti-SEMP1 followed by anti-mouse $F(ab)_2$ labeled with Alexa488 (Molecular Probes). The fluorescence image was recorded.

EXAMPLE 5

Retroviral Construct and Viral Transduction

The SEMP1 retrovirus was generated using a vector containing 1-NGFR cell surface marker as a reporter molecule (Machl, A. W., et al, Cytometry 29 (1997) 371–374). In short, the 5'LTR promotor drives the 1-NGFR marker protein expression. The 3' down-stream located SV40 promotor was substituted by a CMV promotor, which drives the SEMP1 expression. SEMP1 was cloned as ORF with introduction of an ideal Kozak sequence (Kozak, M., Nucleic Acids Res. 15 (1987) 8125–8148). To generate infectious retroviruses, the SEMP1/1-NGFR retroviral plasmid was transfected with lipofectamine (Gibco) into the retrovirus producing, amphotropic HSR BM01 cell line according to the manufactures manual. HSR BM01 high titer retrovirus producing cell clones were generated by FACS cell sorting and subsequent testing of effective transduction rates from conditioned HSRBM01 cell clone supernatants.

This cell line can be used for proving specificity and correct homing of SEMP1 protein, e.g., in oncologically relevant mammary carcinoma cells.

Antibody Specificity

Figure 1:
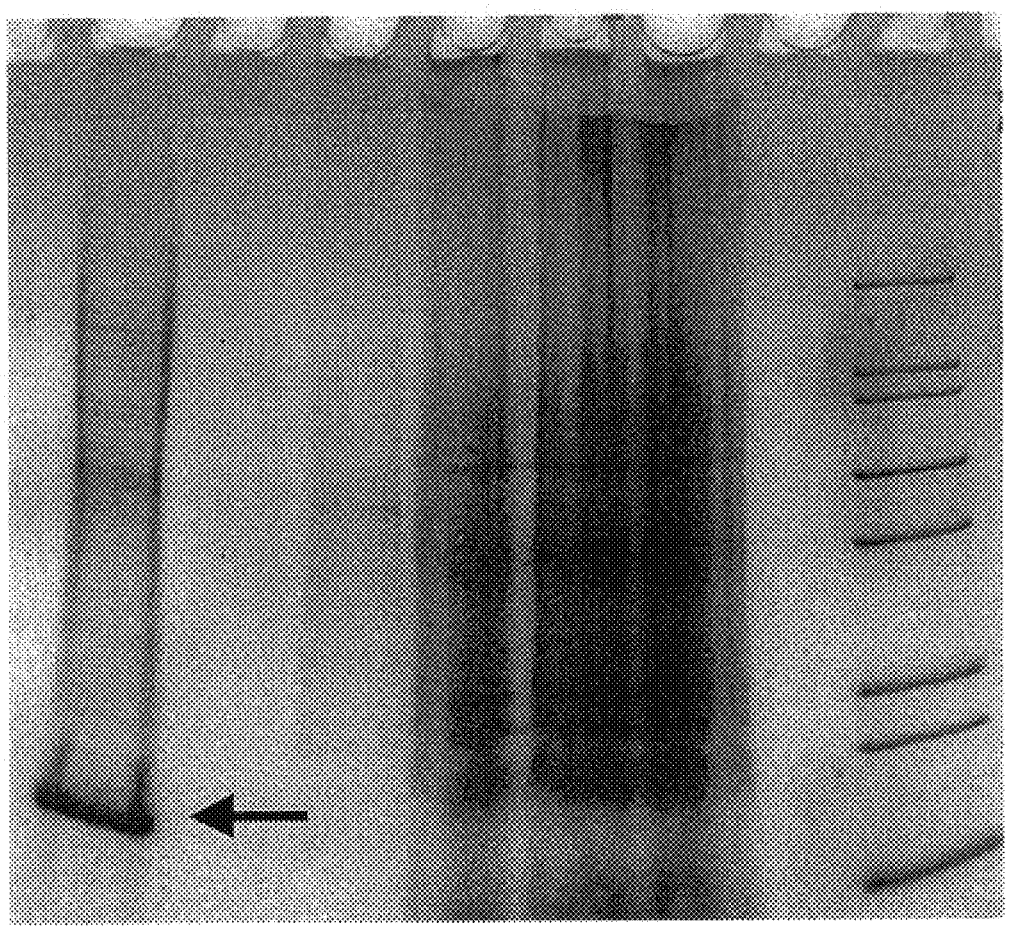
FIG. 1 Purification of SEMP1 protein. His-tagged SEMP1 was expressed in SEMP1-baculovirus infected Sf9 insect cells (Research Diagnostic Inc., NJ, USA, www.researchd.com). His-tag-SEMP1 was purified from crude supernatant of lysed Sf9 cells by column purifications and highest yield and purity was obtained by 200 mM imidazol elution from a Ni-chelat column. The arrow indicates the location of the his-tag-SEMP1 protein.
Figure 2:
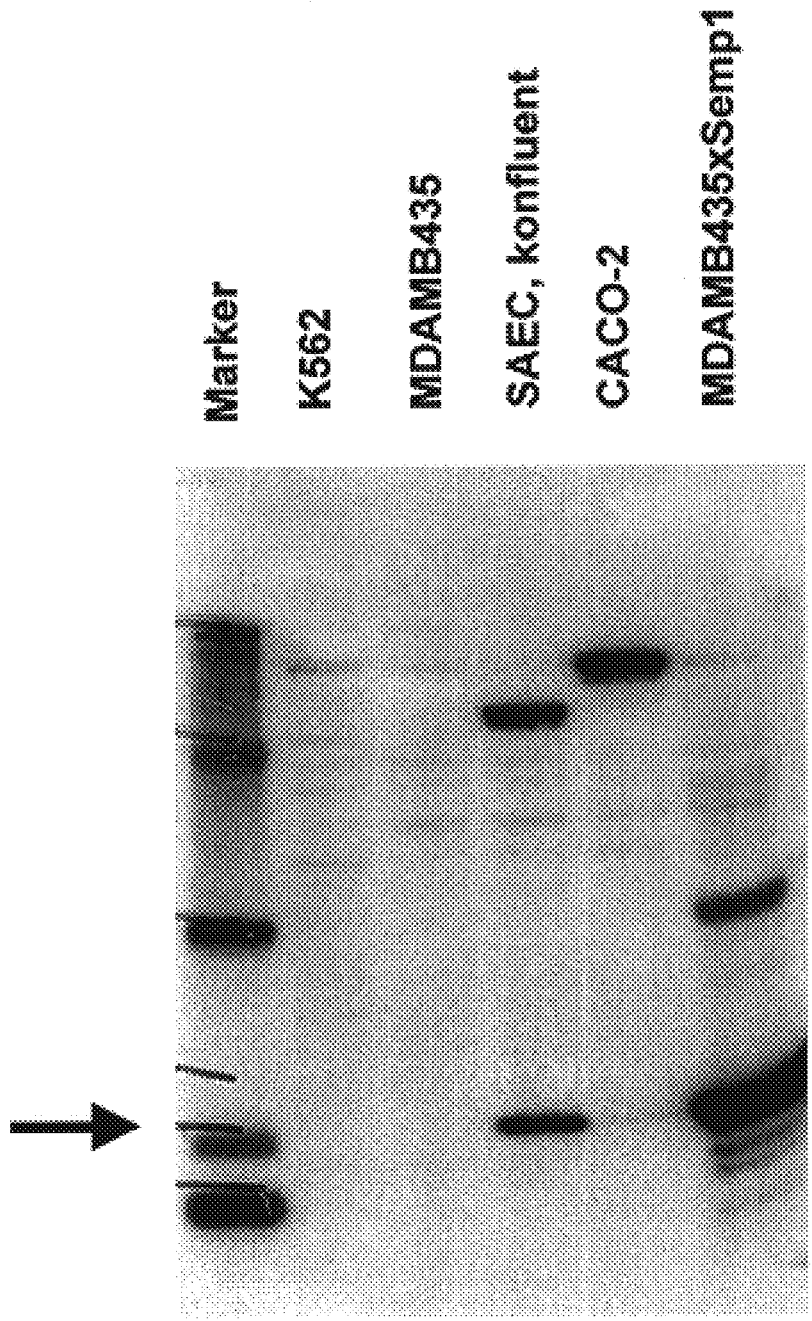
FIG. 2 Specificity and cell dependent SEMP1 expression. Analysis of monoclonal SEMP1 antibody specificity by Western blot analysis. SEMP1 negative (hematopoietic K562, breast cancer MDA-MB435) and positive cells (SAEC—small airway epithelial, adenocarcinoma Caco-2, breast cancer MDA-MB435 transduced with SEMP1 retrovirus) were grown to confluency, lysed and subjected to Western blot analysis. The arrow indicates the position of the native SEMP1 protein.

The SEMP1 specificity of different monoclonal antibodies has been confirmed by Western blot analysis. A typical result is shown in FIG. 2 (arrow, SEMP1 clone c38). Only SEMP1 positive cells like SAEC (small airway epithelial cells) and CACO-2 show a signal at the expected MW of about 23 kD. As expected, the hematopoietic cell line K562 is negative for SEMP1. In addition, the SEMP1 negative breast cancer cell lines MDAMB435 displays no SEMP1 protein band, whereas its retrovirally transduced counterpart MDAMB435xSemp1 displays a strong SEMP1 band. Beside the SEMP1 hybridoma clone c38, a variety of different SEMP1 hybridomas producing monoclonal antibodies against different intra- and extracellular epitops of SEMP1 were obtained.

Figure 3:
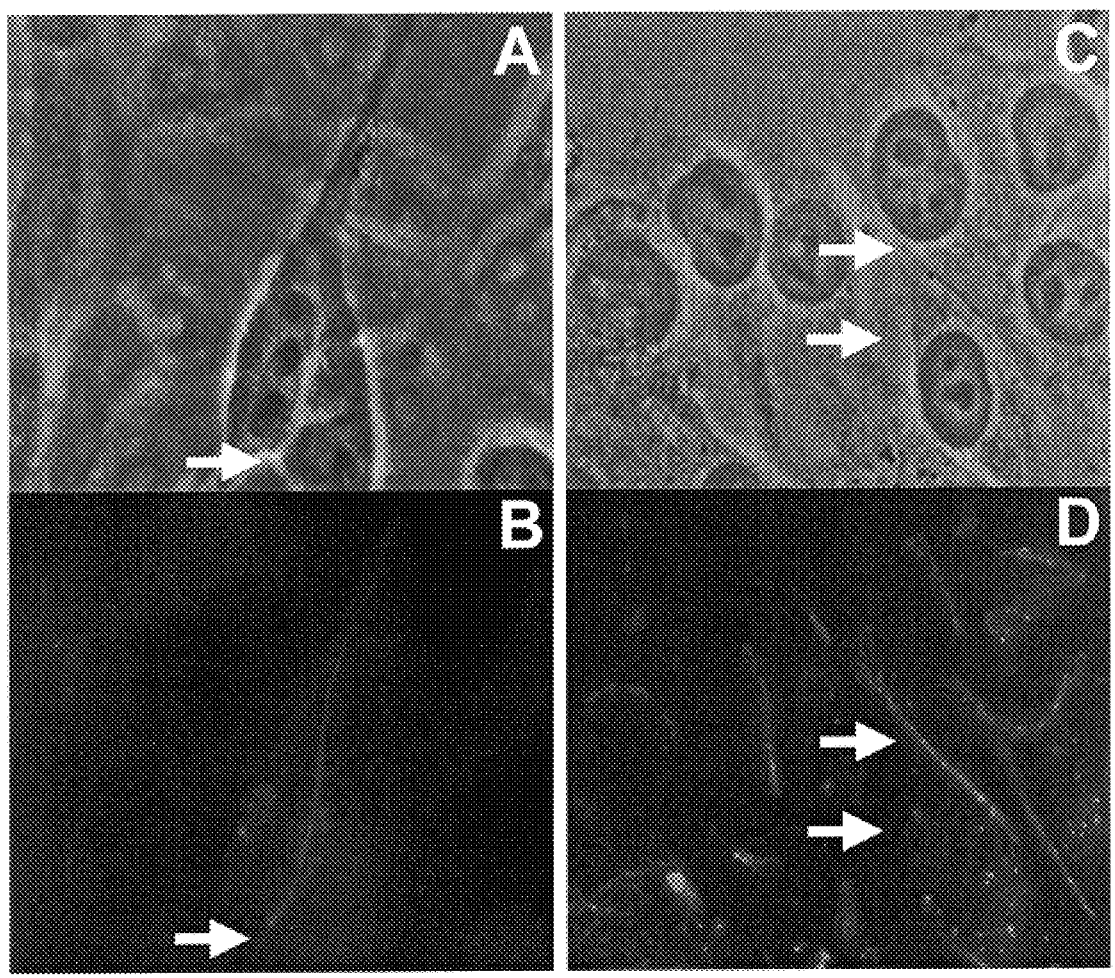
FIG. 3 Expression of SEMP1 in breast cancer cells. SEMP1 expression in SEMP1-transduced MDA-MB435 bulk culture cells was analysed by fluorescence microscopy. The specificity of expression and homing at cell—cell contacts site is indicated by sigmoid staining pattern of SEMP1.

FIG. 3 shows the biological specificity of binding of SEMP1 antibodies. SEMP1 as 4-transmembrane protein is localised only at cell—cell contact sites (arrows, SEMP1 clone c38).

EXAMPLE 6

Epitope Mapping Using Complementary SEMP1 Antibodies

For subsequent screening of epitopes of SEMP1 antibodies an ELISA was performed:
coating of 96-well chambers with his-tagged SEMP1
blocking of chambers with 1% bovine albumin
washing (twice with PBS/0.05% Tween 20)
incubation with hybridoma supernatants containing anti-SEMP1 activity, positive control anti-his-antibody
washing
incubation with secondary antibody conjugated with peroxidase
washing
incubation with peroxidase substrate (ABTS® Solution)

To identify the epitopes of the 66 different antibodies a complementary peptide ELISA was established. For this purpose 44 peptides of the hydrophilic areas of SEMP1 were synthesized and incubated in single reactions during the incubation of the anti-SEMP1 antibody containing supernatants. Using high amounts of the peptide reduces the binding of anti-SEMP1 antibodies with matching epitopes to the his tagged SEMP1.

The reduction of the chromogenic signal was measured in comparison to the not competed supernatants.

EXAMPLE 7

Attempts to Generate SEMP1 Antibodies Using SEMP1 Peptides for Immunization Fusion peptides (QWRIYSYAGD)-KLH (Peptide of SEQ ID NO:1 coupled to keyhole limpet hemocyanin) and KLH-(MKCMKCLEDDEVQKM) (Peptide of SEQ ID NO:2 coupled to keyhole limpet hemocyanin) in Freund's adjuvant were injected into two rabbits. Three subcutaneous dorsal sites were administered, total of 0.1 mg peptide per immunization. Injections were given at weeks 0, 2, 6 and 8. Serum displayed high titer of antibody using the peptides on a dot blot, but did not work at all on cell extracts or in FACS analysis. Therefore, no SEMP1 binding antibodies are generated.

EXAMPLE 8

Enzyme Immunoassay for the Determination of SEMP1 According to the ELISA Principle Reagent 1:
1.25 µg/ml biotinylated Mab clone 3 (preparation according to Peters, J. H., et al., "Monoklonale Antikörper", Springer Verlag, Berlin, 1985, pp. 209–212)
10 mmol/l citrate buffer
47 mmol/l phosphate buffer, pH 6.3
50 mU/ml conjugate of peroxidase and monoclonal antibody clone 5 (prepared according to Wilson, M. B., and Nakane, P. K., 1978, in Immunofluorescence and Related Staining Techniques, W. Knapp, K. Kolubar, G. Wick eds., pp. 215–224, Elsevier/North Holland, Amsterdam; the activity stated refers to peroxidase)

Reagent 2:
100 mmol/l phosphate citrate buffer, pH 4.4
3.2 mmol/l sodium perborate
1.9 mmol/l ABTS® (2,2'-azino-di-[3-ethyl-benzthiazoline sulfonate(6)]

Human sera to which 3, 5, 10 and 25 ng/ml, respectively, of recombinantly produced SEMP1 have been added are used as samples.

The reaction is carried out using small, streptavidin-coated polystyrene tubes (preparation according to EP-A 0 269 092).

Carrying Out the Determination:
0.2 ml sample are incubated in a small tube with 1 ml reagent 1 for 60 minutes at 20–25° C., followed by suction and washing twice with tap water. Subsequently, reagent 2 is added, incubated for 30 minutes at 20–25° C. and the extinction is determined in the photometer at 420 nm. In this way, a standard curve is obtained, allowing the determination of the SEMP1 concentrations of the samples to be examined.

EXAMPLE 9

Detection of SEMP1 in Normal Tissue and Tumor Tissue

Figure 5:
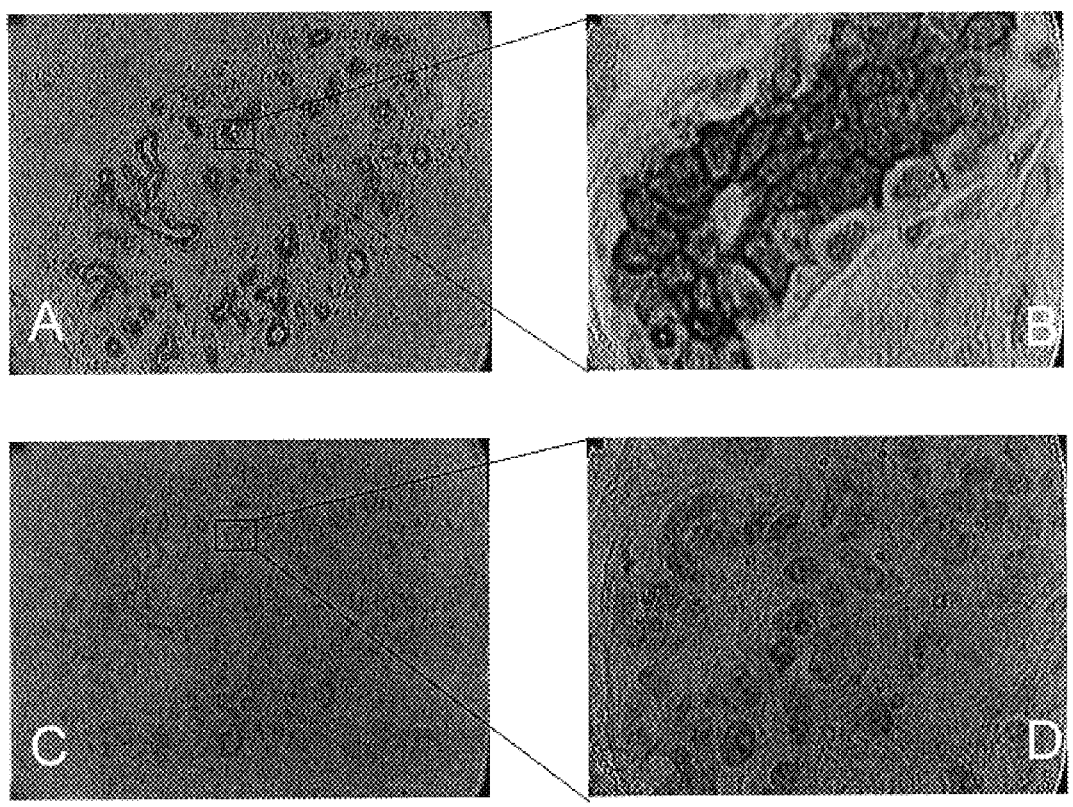
FIG. 5 SEMP1 protein expression in normal human breast tissue. Staining of SEMP1 protein was with anti-SEMP1/anti-mouse-POD and hematoxilin counterstaining (panel A and B). Control staining with secondary antibody anti-mouse-POD is shown in panels C and D. The rectangles in panels A and C indicate the areas shown magnified in panels B and D.

To detect SEMP1 protein in histologic sections, paraffin sections of normal tissue and breast cancer tissue were examined. FIG. 5 shows a section with an anti-SEMP1-antibody staining (FIGS. 5A and B) and with a non-binding antibody (C, D) for control purposes. The anti-SEMP1-antibody according to the invention binds specifically only to the epithelial cells of the different gland structures, whilst the surrounding mesenchymal stroma tissue is not stained. The figure clearly shows that this is a membrane-located staining in which all of the epithelial cells are stained. It is not shown in this figure that, in the mammary gland sections, apart from the lobular structures (epithelial cells) also ductal structures (endothelial cells) can be stained with the antibodies according to the invention.

Figure 6:
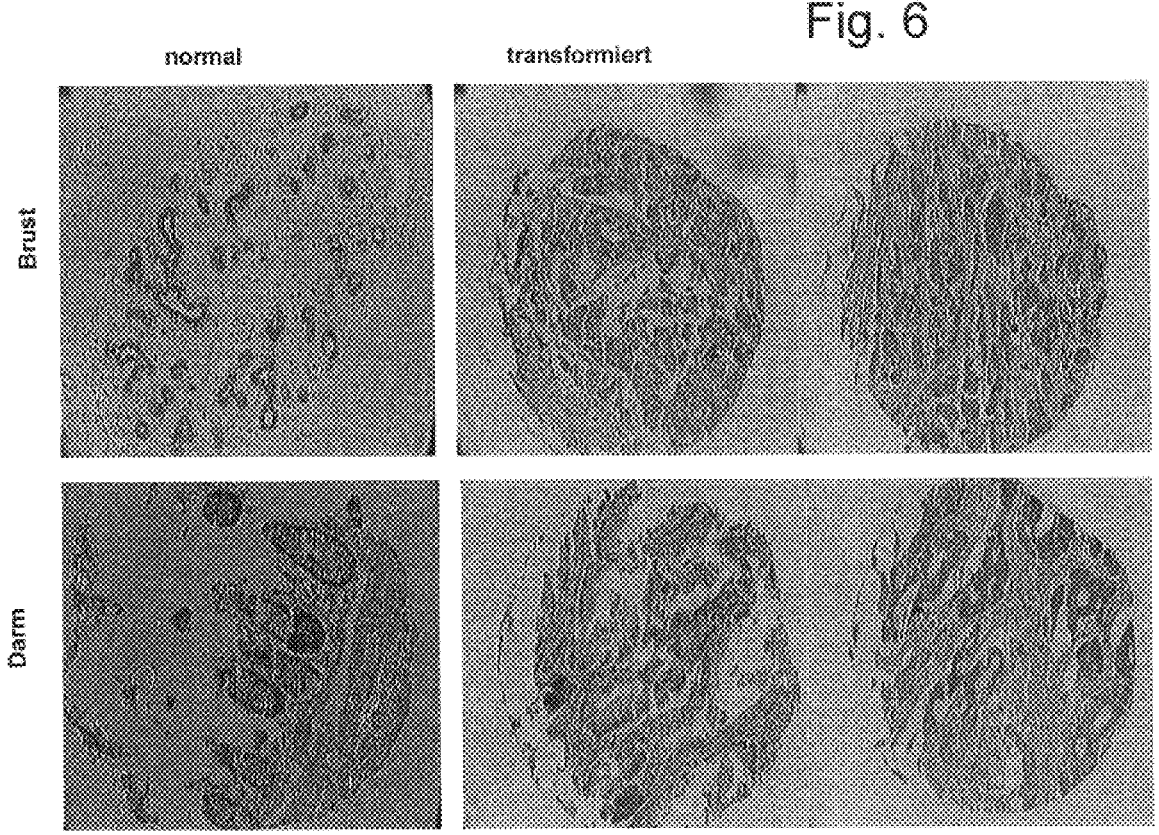
FIG. 6 Comparison of SEMP1 expression in normal breast and colon tissue compared to breast and colon tumor tissue. Staining was as described in FIG. 5. Brust denotes breast; Darm denotes colon; transformiert denotes tumor tissue.

In contrast to this, expression of SEMP1 in tumor tissue is significantly lower than in normal tissue. This is shown in FIGS. 6 and 7. Whereas in normal tissue from breast or colon, SEMP1 is found especially on the membrane part of the epithelial cells, in tumor tissue, some staining was found for the membrane and the cytoplasm. However, staining in tumor tissue was considerably lower than in normal tissue.

FIG. 7 shows a comparison of a section of normal breast tissue with eight sections of breast tumor tissue. FIG. 7 shows that especially lobular structures are stained. In all cases, the staining is found at the membrane. In none of the sections of breast tumor tissue a membrane-located staining could be detected as was found in normal breast tissue. For breast tumor tissue, the staining is always a low uniform cytosolic staining.

These experiments demonstrate that anti-SEMP1 antibodies according to the invention can be effectively used for the diagnosis of the status of tight junction of cells and therefore are a valuable marker for tumorigenesis and/or tumor progression.

LIST OF REFERENCES

Barry, M. A., et al., Biotechniques 16 (1994) 616–618 and 620
Bessler, W. G., et al., Immunobiol. 170 (1985) 239–244
Bird, R. E., et al., Science 242 (1988) 423–426
Borrebaeck, C. A. K., et al., Proc. Natl. Acad. Sci. USA 85 (1988) 3995–3999
Borrebaeck, C. A. K., Immunol. Today 9 (1988) 355–359
Chochand-Prillet, B., et al., Ultrastruct. Pathol. 22 (1998) 413–420
Cianfriglia, M., et al., Hybridoma 2 (1993) 451–457
Davis, H. L., Curr. Opin. Biotechnol. 8 (1997) 635–646
Davis, H. L., et al., Hum. Mol. Genet. 2 (1993) 1847–1851
Davis, H. L., et al., Vaccine 12 (1994) 1503–1509
E. Harlow and D. Lane, Antibodies: A Laboratory Manual, Cold Spring Harbor Press (1988)
EP-A 0 269 092
Furuse, M., et al., J. Cell Biol. 141 (1998) 1539–1550
Furuse, M., et al., J. Cell Biol. 143 (1998) 391–401
Furuse, M., et al., J. Cell Biol. 147 (1999) 891–903
Glassy, M. C., and Dillman, R. O., Mol. Biother. 1 (1988) 7–13
Griffiths, A. D., et al., EMBO J. 12 (1993) 725–734
Harlow E. and Lane D., "Antibodies—A Laboratory Manual", Cold Spring Harbor Laboratory (1988)
Hood et al., Immunology, Benjamin N.Y., 2nd edition (1984)
Houston et al., PNAS USA 85 (1988) 5879–5883
Hunkapiller, T., and Hood, L., Nature 323 (1986) 15–16
Introduction to Protein Structure, C. Brandon and J. Tooze, Garland Publishing, New York (1981)
Jung, G., et al., Angewandte Chemie 97 (1985) 883–885
Kozak, M., Nucleic Acids Res. 15 (1987) 8125–8148
Lowrie, D. B., Nat. Med. 4 (1998) 147–148
Machl, A. W., Cytometry 29 (1997) 371–374
Morrison, S. L., Annu. Rev. Immunol. 10 (1992) 239–265
Peters, J. H., et al., "Monoklonale Antikorper", Springer Verlag, Berlin, 1985, pp. 209–212
Porvaznik, M., et al., J. Supramol. Struct. 10 (1979) 13–30
Proteins, Structures and Molecular Principles, Creighton (editor), W.H. Freeman and Company, New York (1984)
Rothman, P., et al., Mol. Cell. Biol. 10 (1990) 1672–1679
Sambrook et al., Molecular Cloning: A Laboratory Manual, 2nd edition (1989), Cold Spring Harbor, N.Y.
Soler, A. P., et al., Carcinogenesis 20 (1999) 1425–1431
Sustained and Controlled Release Drug Delivery Systems, J. R. Robinson, ed., Marcel Dekker, Inc., New York, 1978
Swift, J. G., et al., J. Submicrosc. Cytol. 15 (1983) 799–810
Swisshelm, K. A., et al., Gene 226 (1999) 285–295
Thornton, J. M., et al., Nature 354 (1991) 105–106
Ulivieri, C., et al., J. Biotechnol. 51 (1996) 191–194
Wilson, M. B., and Nakane, P. K., 1978, in Immunofluorescence and Related Staining Techniques, W. Knapp, K. Kolubar, G. Wick eds., pp. 215–224, Elsevier/North Holland, Amsterdam
Winter, G., and Milstein, C., Nature 349 (1991) 293–299
WO 95/06723
WO 99/00010
WO 99/60143
Woo, P. L., et al., J. Biol. Chem. 274 (1999) 32818–32828

What is claimed is:

1. An antibody secreted from a cell line selected from the group consisting of cell lines DSM ACC2458, DSM ACC2459, DSM ACC2460, DSM ACC2461, DSM ACC2462, and DSM ACC2463.

2. An Fab, Fab', or F(ab)'$_2$ fragment of an antibody secreted from a cell line selected from the group consisting of cell lines DSM ACC2458, DSM ACC2459, DSM ACC2460, DSM ACC2461, DSM ACC2462, and DSM ACC2463.

3. An antibody containing a variable region and a constant region, wherein said variable region is the variable region of an antibody secreted from a cell line selected from the group consisting of cell lines DSM ACC2458, DSM ACC2459, DSM ACC2460, DSM ACC2461, DSM ACC2462, and DSM ACC2463 and wherein the variable region is linked to a constant region of a human antibody.

4. An antibody containing a variable region and a constant region, wherein said variable region is the variable region of an antibody secreted from a cell line selected from the group consisting of cell lines DSM ACC2458, DSM ACC2459, DSM ACC2460, DSM ACC2461, DSM ACC2462, and DSM ACC2463, and wherein said variable region is modified by replacing part or all of the non-SEMP1 binding sequences with the corresponding sequences from a human variable region and wherein the variable region is linked to a constant region of a human antibody.

5. An antibody according to claim 4, wherein the antibody is a CDR grafted antibody.

6. A cell line selected from the gorup consisting of DSM ACC2458, DSM ACC2459, DSM ACC2460, DSM ACC2461, DSM ACC2462, and DSM ACC2463.

* * * * *